United States Patent [19]

Wada et al.

[11] Patent Number: 5,797,893
[45] Date of Patent: Aug. 25, 1998

[54] ABSORBING AGENT COMPOSITION, ABSORBENT MATERIAL, AND ABSORBENT PRODUCT CONTAINING ABSORBENT MATERIAL

[75] Inventors: Katsuyuki Wada, Himeji; Kunihiko Ishizaki, Suita; Kinya Nagasuna, Himeji, all of Japan

[73] Assignee: Nippon Shokubai Co., Ltd., Osaka, Japan

[21] Appl. No.: 703,882

[22] Filed: Aug. 27, 1996

[30] Foreign Application Priority Data

Sep. 1, 1995 [JP] Japan .................................. 7-224928
Dec. 12, 1995 [JP] Japan .................................. 7-323305

[51] Int. Cl.$^6$ .................................. A61F 13/15; A61F 13/20
[52] U.S. Cl. .................................. 604/372; 604/368
[58] Field of Search .................................. 604/368, 369, 604/372, 374, 375

[56] References Cited

U.S. PATENT DOCUMENTS

| | | | |
|---|---|---|---|
| 4,666,975 | 5/1987 | Yamasaki et al. | 524/733 |
| 5,147,343 | 9/1992 | Kellenberger | 604/368 |
| 5,149,335 | 9/1992 | Kellenberger et al. | 604/372 |

FOREIGN PATENT DOCUMENTS

| | | |
|---|---|---|
| 0 532 002 A1 | 3/1993 | European Pat. Off. . |
| 63-21902 A | 1/1988 | Japan . |
| 63-99861 A | 5/1988 | Japan . |

*Primary Examiner*—John G. Weiss
*Assistant Examiner*—Ki Yong O
*Attorney, Agent, or Firm*—Kubovcik & Kubovcik

[57] ABSTRACT

An absorbing agent composition exhibiting excellent properties (absorbing properties), such as capabilities of maintaining high liquid diffusion and a constant absorbing capacity per unit weight, even when an amount of an absorbent resin is increased in percent by weight based on the weight of the absorbing agent composition, and an absorbent material containing such an absorbing agent composition and an absorbent product containing the absorbent material. The absorbing agent composition has a diffusing absorbency index under pressure of 1.5 g/g·min or higher with respect to a physiological saline solution under a load of 20 g/cm$^2$. The absorbent material contains at least 40 weight percent absorbing agent composition based on the weight of the absorbent material. The absorbent product comprises an absorbent layer containing the absorbent material sandwiched by a liquid permeable sheet and a liquid impermeable sheet. The diffusing absorbency index under pressure is calculated by a device used for measuring the diffusing absorbency under pressure, that is, a weight of a physiological saline solution absorbed by the absorbing agent composition placed in a supporting cylinder for 60 minutes since the supporting cylinder is placed on a sheet with a weight is measured in time series using a balance.

12 Claims, 4 Drawing Sheets

ABSORBING AGENT COMPOSITION, ABSORBENT MATERIAL, AND ABSORBENT PRODUCT CONTAINING ABSORBENT MATERIAL

FIELD OF THE INVENTION

The present invention relates to an absorbing agent composition suited for use in sanitary goods, such as paper diapers (disposal diapers), sanitary napkins, incontinence pads, an absorbent material, and an absorbent product containing the absorbent material.

BACKGROUND OF THE INVENTION

Recently, an absorbent resin is used extensively in sanitary goods, such as paper diapers, sanitary napkins, incontinence pads, to absorb body fluids.

Examples of such absorbent resins include: a partially neutralized crosslinked polymer of polyacrylic acid (Japanese Laid-Open Patent Publication Nos. 84304/1980 (Tokukaisho 55-84304), 108407/1980 (Tokukaisho 55-108407), and 133413/1980 (Tokukaisho 55-133413)); a hydrolyzed graft polymer of starch-acrylonitrile (Japanese Laid-Open Patent Publication No. 43995/1971 (Tokukaisho 46-43995); a neutralized graft polymer of starch-acrylic acid (Japanese Laid-Open Patent Publication No. 125468/1976 (Tokukaisho 51-125468)); a saponified copolymer of vinyl acetate-acrylic ester (Japanese Laid-Open Patent Publication No. 14689/1977 (Tokukaisho 52-14689)); a hydrolyzed copolymer of acrylonitrile or acrylamide, or a crosslinked product thereof (Japanese Laid-Open Patent Publication No. 15959/1978 (Tokukaisho 53-15959)); and a crosslinked polymer of cationic monomer (Japanese Laid-Open Patent Publication Nos. 154709/1983 (Tokukaisho 58-154709) and 154710/1983 (Tokukaisho 58-154710)).

Notable properties of the absorbent resin include absorbing capacity and absorbency under pressure when it is in contact with an aqueous liquid like a body fluid, gel strength, and absorbing power of absorbing liquid from a base material containing an aqueous liquid, etc. Conventionally, the absorbent resins having some of the above-mentioned properties which show desirable properties (absorption properties) in their applications of paper diaper, sanitary napkin, etc., as well as absorbent materials and the absorbent product using such absorbent resins have been proposed.

Examples of such absorbent resins, absorbent materials and absorbent products include: an absorbent resin disclosing a combination of a specific gel capacity, shear modulus and an extraction polymer content (U.S. Pat. No. 4,654,039); an absorbent resin having predetermined ranges of absorbing capacity, absorbing rate, and gel strength, and paper diapers or sanitary napkins using such an absorbent resin (Japanese Laid-Open Patent Publication Nos. 185550/1985 (Tokukaisho 60-185550), 185551/1985 (Tokukaisho 60-185551), and 185804/1985 (Tokukaisho 60-185804)); paper diapers using an absorbent resin having predetermined ranges of absorbing capacity, absorbing rate, and gel stability (Japanese Laid-Open Patent Publication No. 185805/1985 (Tokukaisho 60-185805)); an absorbent product containing an absorbent resin having predetermined ranges of absorbing capacity, absorbing power, and water-soluble content (Japanese Laid-Open Patent Publication No. 21902/1988 (Tokukaisho 63-21902)); absorbent sanitary goods containing an absorbent resin having predetermined ranges of absorbing capacity, absorbing capacity under pressure and gel breaking strength (Japanese Laid-Open Patent Publication No. 99861/1988 (Tokukaisho 63-99861)); a paper diaper containing an absorbent resin having predetermined ranges of absorbing capacity and absorbency under pressure (Japanese Laid-Open Patent Publication No. 34167/1990 (Tokukaihei 2-34167)); an absorbing agent containing an absorbent resin having predetermined ranges of absorbing capacity under pressure and particle diameter (European Patent No. 339,461); an absorbent structure including at least a predetermined amount of absorbent resin having predetermined ranges of absorbing rate and absorbing capacity under pressure in a short period of time (European Patent No. 443,627); and a synthetic absorbing material having at least a predetermined amount of absorbent resin having predetermined ranges of deformation under load and wicking index (European Patent No. 532,002).

Recent sanitary goods, such as paper diapers and sanitary napkins, have been improved in terms of performance and thinness, and accordingly, an amount of absorbent resin used in the sanitary goods per sheet, or percent by weight of the absorbent resin based on the weight of the absorbent material mainly composed of the absorbent resin and hydrophilic fibers (hereinafter simply referred to as a resin concentration) has been increasing. Namely, by reducing the amount of hydrophilic fiber having a small bulk specific gravity and increasing the amount of the absorbent resin having a large bulk specific gravity, the ratio of the absorbent resin in the absorbent material is raised, and a thinner sanitary material can be achieved without reducing the absorbing capacity.

However, earnest researches have been made by the inventors of the present invention in order to increase the absorbing amount of the sanitary material, for example, by increasing the resin concentration in the absorbent material. As a result, the inventors have found that the absorbent material having a higher resin concentration than conventional absorbent material cannot be used without having problems such as leakage of aqueous liquid from the sanitary goods, etc., only by controlling the described absorbing capacity, absorbency under pressure, gel strength, absorbing capacity, etc. For example, as to the absorbent resin which has been viewed with interest in which only absorbing capacity under pressure is large, by raising the resin concentration, the liquid dispersibility of the absorbent material is significantly reduced.

Further researches have been made by the inventors on absorbing properties of the absorbent material having higher resin concentration than conventional absorbent material. As a result, they have found that in the case of using a mixture of a known absorbent resin, a hydrophilic fiber is used as an absorbent material, although when a resin concentration is low, the absorbent material shows a predetermined level of absorbing properties, when a resin concentration is above 40 percent by weight, such unpreferable conditions that the liquid dispersibility is rapidly lowered, the absorbing capacity of weight per unit of the absorbent material is lowered, etc., would occur. In short, the absorbent material made of a mixture of a known absorbent resin and hydrophilic fibers causes the problems explained above.

SUMMARY OF THE INVENTION

It is therefore an object of the present invention to provide an absorbing agent composition such that exhibits excellent properties (absorbing properties), such as capabilities of maintaining high liquid diffusion and a constant absorbing capacity per unit weight, even when an absorbent resin is increased in percent by weight based on the absorbing agent composition, as well as an absorbent material containing such an absorbing agent composition and an absorbent product containing the absorbent material.

To fulfill the above object, the inventors of the present invention continued the steady and persistent studies on absorbing agent composition, absorbent material, and absorbent product containing the absorbent material. In the meantime, the inventors discovered a unique property value, that is, a diffusing absorbency index under pressure, which is suitably used to measure liquid diffusion when the absorbing agent composition is absorbing an aqueous liquid under predetermined conditions. The absorbing agent composition having a higher diffusing absorbency index under pressure can be obtained by mixing an absorbent resin having at least predetermined diffusing absorbency under pressure and a specific compound, or surface crosslinking such an absorbent resin under specific conditions.

The inventors discovered that an absorbing agent composition having a higher diffusing absorbency index under pressure can steadily absorb an aqueous liquid supplied in bulk even if the absorbent resin is increased in percent by weight, and that such an absorbing agent composition exhibits excellent properties (absorbing properties), such as capabilities of maintaining high liquid diffusion and a constant absorbing capacity per unit weight. The inventors also discovered that using such an absorbing agent composition makes it possible to obtain an absorbent material and an absorbent product with excellent absorbing properties.

To fulfill the above object, the absorbing agent composition of the present invention is characterized by having a diffusing absorbency index under pressure of 1.5 g/g·min or higher with respect to a 0.9 weight percent sodium chloride solution under a load of 20 g/cm$^2$.

According to the above arrangement, the above absorbing agent composition can steadily absorb an aqueous liquid supplied in bulk, and even if the absorbent resin is increased in percent by weight, the absorbing agent composition exhibits excellent properties (absorbing properties), such as capabilities of maintaining high liquid diffusion and a constant absorbing capacity per unit weight.

Also, to fulfill the above object, the absorbent material of the present invention is characterized by including at least one of the above-specified absorbing agent compositions.

According to the above arrangement, it has become possible to provide an absorbent material which can steadily absorb an aqueous liquid supplied in bulk while exhibiting excellent absorbing properties, such as capabilities of maintaining high liquid diffusion and a constant absorbing capacity. The absorbent material of the present invention can be used suitably in making further improved and thinner absorbent products, such as sanitary goods including paper diapers, sanitary napkins, incontinence pads, etc.

Further, to fulfill the above object, the absorbent product of the present invention is characterized by comprising an absorbent layer containing the above absorbent material sandwiched by a liquid permeable sheet and a liquid impermeable sheet.

According to the above arrangement, it has become possible to provide an absorbent product, such as sanitary goods, which can steadily absorb an aqueous liquid supplied in bulk and exhibits excellent absorbing properties, such as capabilities of maintaining high liquid diffusion and a constant absorbing capacity.

For a fuller understanding of the nature and advantages of the invention, reference should be made to the ensuing detailed description taken in conjunction with the accompanying drawings.

DESCRIPTION OF THE EMBODIMENTS

Figure 1:
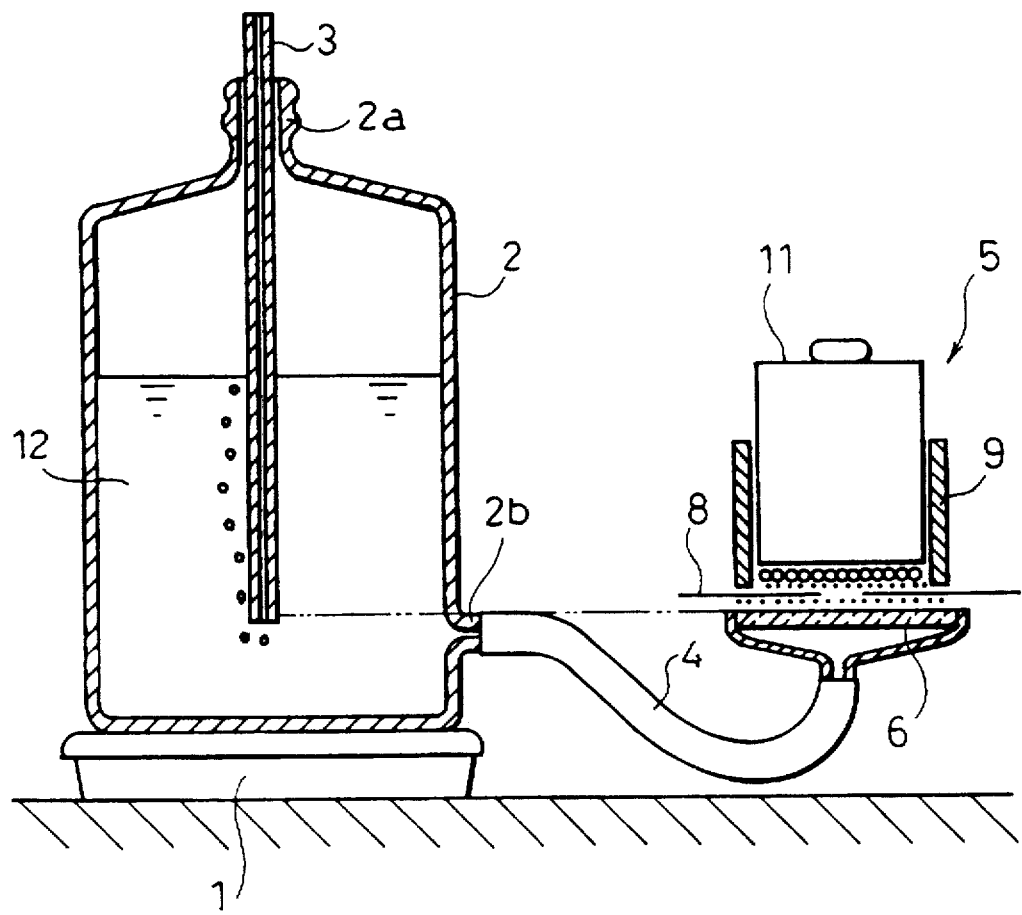
FIG. 1 is a schematic cross section of a device measuring diffusing absorbency under pressure indicating one of the properties of an absorbing agent composition of the present invention.

The diffusing absorbency index under pressure referred herein is a new property value suitably used to evaluate liquid diffusion of the absorbent resin or absorbing agent composition (hereinafter, the explanation is carried out on the basis of the absorbent resin for the explanation's convenience) while the same is absorbing an aqueous liquid when the basis weight of the absorbent resin is high and resin particles are linked tightly to each other by an external force. The diffusing absorbency index under pressure is calculated using maximum absorbency under pressure at which the absorbent resin absorbs an aqueous liquid along the direction of the absorbent resin layer (hereinafter, referred to as the lateral direction) under predetermined conditions, the details of which will be given below.

The diffusing absorbent index under pressure indicates how steadily the absorbent resin absorbs the aqueous liquid and how uniform and fast the absorbent resin diffuses the aqueous liquid in the lateral direction. The diffusion (liquid diffusion and liquid transmissivity) of the aqueous liquid in the lateral direction is particularly an import factor in absorbing a great amount of aqueous liquid. This evaluation makes it easier to predict the absorbing behavior of the absorbent resin in an absorbent material, for example, the one mainly composed of the absorbent resin and hydrophilic fibers, especially the one having a high resin concentration. The structure of the absorbent material will be described below.

The diffusing absorbency under pressure used herein as a preferable property value for the absorbing agent composition is a property value used to evaluate an absorbing capacity of the absorbing agent composition in consideration of diffusion of the aqueous liquid when the basis weight of the absorbent resin is high and resin particles are linked tightly to each other by an external force. The diffusing absorbency under pressure is calculated using a value measured under predetermined conditions after a predetermined period, for example, 60 minutes, since the absorption started, which will be explained below.

Many of the foregoing prior art documents incorporate the evaluation on the absorbing rate. However, none of them includes the evaluation on the maximum absorbing rate under pressure while an aqueous liquid is being diffused in the lateral direction. In other words, the evaluation was carried out only in a direction intersecting with the resin layer direction (hereinafter, referred to as the longitudinal direction) in these documents, that is to say, the evaluation was carried out only in the shorter distance the aqueous liquid moves. Thus, the absorbing behavior of the absorbent material in the diapers, etc. adopting the absorbent material having a high resin concentration, can not be predicted accurately from the result of the conventional evaluations.

The absorbing agent composition of the present invention has a diffusing absorbency index under pressure of 1.5 g/g·min or higher, and more preferably, 3.0 g/g·min or higher, with respect to a 0.9 weight percent sodium chloride solution under a load of 20 g/cm$^2$. A preferred absorbing agent composition further has diffusing absorbency under pressure of 25 g/g or higher with respect to a 0.9 weight percent sodium chloride solution under a load of 20 g/cm$^2$ after 60 minutes since the absorption started. Further, the absorbing agent composition may include a non-volatile water-soluble compound.

To be more specific, the absorbing agent composition of the present invention can be obtained by adding microscopic water-insoluble inorganic powders (hereinafter referred to as water-insoluble inorganic powders) to an absorbent resin having diffusing absorbency under pressure of 25 g/g or higher with respect to a 0.9 weight percent sodium chloride solution under a load of 20 g/cm$^2$ after 60 minutes since the absorption started. Alternatively, the absorbing agent composition of the present invention can be obtained by adding a polyamine compound whose weight average molecular weight (Mw) is 5,000 or greater (hereinafter, referred to as polyamine compound) to an absorbent resin having diffusing absorbency under pressure of 25 g/g or higher with respect to a 0.9 weight percent sodium chloride solution under a load of 20 g/cm$^2$ after 60 minutes since the absorption started. Also, the absorbing agent composition of the present invention can be obtained by adding the water-insoluble inorganic powders and polyamine compound to an absorbent resin having diffusing absorbency under pressure of 25 g/g or higher with respect to a 0.9 weight percent sodium chloride solution under a load of 20 g/cm$^2$ after 60 minutes since the absorption started.

Further, the absorbing agent composition of the present invention can be obtained by surface crosslinking an absorbent resin through heat treatment using a surface crosslinking agent made of a mixture of specific crosslinking agents, and mixing the surface crosslinked absorbent resin and the surface crosslinking agent to subject the resulting mixture to heat treatment again. The surface crosslinking agent will be detailed below.

A preferred absorbent resin is, for example, an absorbent crosslinked polymer containing a carboxyl group. The absorbent crosslinked polymer is obtained by, for example, letting a hydrophilic unsaturated monomer mainly composed of acrylic acid or the salt thereof undergo (co)polymerization (hereinafter, referred to as polymerization). Of all the preferred absorbent crosslinked polymers, the more preferable is a crosslinked polymer of the salt of polyacrylic acid. It is further preferable that 50–90 mole percent acid radicals of the above crosslinked polymer are neutralized by alkali metal salt, ammonium salt, amine salt, or the like.

The above absorbent resin may be known absorbent resins, such as partially neutralized crosslinked polymer of polyacrylic acid (U.S. Pat. Nos. 4,625,001, 4,654,039, 5,250,640, and 5,275,773, and Europe Patent No. 456136), a partially neutralized crosslinked graft polymer of starch-acrylonitrile (U.S. Pat. No. 4,076,663), a copolymer of isobutylene-maleic acid (U.S. Pat. No. 4,389,513), a saponified copolymer of vinyl acetate-acrylic acid (U.S. Pat. No. 4,124,748), a hydrolyzed (co)polymer of acrylamide (U.S. Pat. No. 3,959,569), and a hydrolyzed polymer of acrylonitrile (U.S. Pat. No. 3,935,099).

The above hydrophilic unsaturated monomer may optionally contain unsaturated monomers other than acrylic acid and the salt thereof (hereinafter referred to as other monomers). Examples of the other monomers include, but are not limited to:

anionic unsaturated monomers, such as methacrylic acid, maleic acid, vinylsulfonic acid, styrenesulfonic acid, 2-(meth)acrylamide-2-methylpropanesulfonic acid, 2-(meth)acryloylethanesulfonic acid, 2-(meth)acryloylpropanesulfonic acid, and salts of these acids;

nonionic unsaturated monomers containing hydrophilic groups, such as acrylamide, methacrylamide, N-ethyl (meth)acrylamide, N-n-propyl(meth)acrylamide, N-isopropyl(meth)acrylamide, N,N-dimethyl(meth) acrylamide, 2-hydroxyethyl(meth)acrylate, 2-hydroxypropyl(meth)acrylate, methoxypolyethylene glycol (meth)acrylate, polyethylene glycol mono(meth) acrylate, vinylpyridine, N-vinylpyrrolidone, N-acryloylpiperidine, and N-acryloylpyrrolidine;

cationic unsaturated monomers, such as N,N-dimethylaminoethyl(meth)acrylate, N,N-diethylaminoethyl(meth)acrylate, N,N-dimethylaminopropyl(meth)acrylate, N,N-dimethylaminopropyl(meth)acrylamide, and quaternary salts thereof; etc.

An amount of use of these monomers is preferably 30 percent by mole or less, and more preferably 10 percent by mole or less, based on the entire hydrophilic unsaturated monomer.

A precursor of the absorbent resin (hereinafter, referred to as the absorbent resin precursor) obtained by polymerizing the hydrophilic unsaturated monomer contains a carboxyl group. When obtaining the absorbent resin precursor, it is preferable to introduce the crosslinking structure inside of the same using an internal crosslinking agent. The internal crosslinking agent is not especially limited and may be any compound having a plurality of polymeric unsaturated groups and/or reactive groups in one molecule. In other words, the internal crosslinking agent may be any compound having a plurality of substituent groups copolymerizable and/or reactive with the hydrophilic unsaturated monomer in one molecule. Alternatively, the hydrophilic unsaturated monomer may be a self-crosslinking compound that forms the crosslinking structure without using the internal crosslinking agent.

Examples of the internal crosslinking agent include, but are not limited to:

N,N'-methylenebis(meth)acrylamide, (poly)ethylene glycol di(meth)acrylate, (poly)propylene glycol di(meth) acrylate, trimethylolpropane tri(meth)acrylate, trimethylolpropane di(meth)acrylate, glycerol tri(meth)acrylate, glycerin acrylate methacrylate, ethylene oxide denatured trimethylolpropane tri(meth)acrylate, pentaerythritol tetra (meth)acrylate, dipentaerythritol hexa(meth)acrylate, triallyl cyanurate, triallyl isocyanurate, triallyl phosphate, triallylamine, poly(meth)allyloxyalkane, (poly)ethylene glycol diglycidyl ether, glycerol diglycidyl ether, ethylene glycol, polyethylene glycol, propylene glycol, glycerin, pentaerythritol, ethylenediamine, polyethyleneimine, glycidyl(meth)acrylate, etc. One member or a mixture of two or more members selected from these internal crosslinking agents can be used effectively. Of all these internal crosslinking agents, those having a plurality of polymeric unsaturated groups in one molecule can further improve the absorbing properties of the resulting absorbent resin.

A preferred amount of use of the internal crosslinking agent with respect to the hydrophilic unsaturated monomer is in a range between 0.005 percent by mole and 3 percent by mole, and more preferably, between 0.01 percent by mole and 1.5 percent by mole. Neither an amount less than 0.005 percent by mole nor an amount more than 3 percent by mole may result in an absorbent resin with desired absorbing properties.

When obtaining the absorbent resin precursor by polymerizing the hydrophilic unsaturated monomer, the followings or the like may be added to the reactant:

a hydrophilic polymer, such as starch, a derivative of starch, cellulose, a derivative of cellulose, polyvinyl alcohol, polyacrylate, polyacrylic acid, crosslinked polyacrylate, and crosslinked polyacrylic acid;

a chain transfer agent, such as hypophosphite and hypophosphorous acid; and water soluble or water dispersible surfactant.

A polymerizing method of the hydrophilic unsaturated monomer is not especially limited. For example, known methods, such as solution polymerization, reverse phase suspension polymerization, bulk polymerization, and precipitation polymerization can be adopted. Of all these polymerization methods, methods in which a water solution of the hydrophilic unsaturated monomer is polymerized, that is, the solution polymerization and reverse phase suspension polymerization, are particularly preferred in terms of readiness in controlling the polymerization reaction and properties of the resulting absorbent resin. The reaction conditions, such as reaction temperature and time, are not especially limited, and can be set arbitrary depending on the kinds of the hydrophilic unsaturated monomers.

The hydrophilic unsaturated monomer can be also polymerized by known methods, for example, those disclosed in U.S. Pat. Nos. 4,625,001, 4,769,427, 4,873,299, 4,093,776, 4,367,323, 4,446,261, 4,683,274, 4,690,996, 4,721,647, 4,738,867, and 4,748,076.

When polymerizing the hydrophilic unsaturated monomer, a radical polymerization initiator, such as potassium persulfate, ammonium persulfate, sodium persulfate, t-butylhydro peroxide, hydrogen peroxide, 2,2'-azobis(2-amidinopropane)dihydrochloride, activation energy rays, such as UV rays and electron beams, or the like can be used. when the oxidizing radical polymerization initiator is used, the hydrophilic unsaturated monomer may undergo redox polymerization using a reducing agent, such as sodium sulfite, sodium hydrogen sulfite, ferrous sulfate, and L-ascorbic acid. A preferable amount of use of the polymerization initiator is in a range between 0.001 percent by mole and 2 percent by mole, and more preferably, between 0.01 percent by mole and 0.5 percent by mole.

The resulting absorbent resin precursor obtained by any of the above polymerization methods is, for example, sieved to a predetermined particle size. The absorbent resin precursor may be spherical, leaflet, undefined, fibriform, granular, bar-wise, substantially spherical, flat, etc.

The absorbent resin of the present invention, having diffusing absorbency under pressure of 25 g/g or higher with respect to a 0.9 weight percent sodium chloride solution under a load of 20 g/cm$^2$ after 60 minutes since the absorption started, is obtained by surface crosslinking the above absorbent resin precursor in the presence of a specific surface crosslinking agent. An example method of obtaining the absorbent resin is disclosed in U.S. patent application Ser. No. 08/571,960. To be more specific, the absorbent resin precursor is sieved to have an average particle size between 200 μm and 600 82 m and to contain up to 10 weight percent particles having a diameter smaller than 106 μm. Then, the absorbent resin precursor is subject to heat treatment in the presence of a mixture of the first crosslinking agent and second crosslinking agent, which will be described below. According to the above method, the crosslinking density of the absorbent resin is increased on the surface than the inside, thereby making it possible to obtain an absorbent resin having high diffusing absorbency under pressure. When the absorbent resin precursor has an average particle diameter outside of the above range between 200 μm and 600 μm, or the particles having a diameter smaller than 106 μm exceeds 10 percent by weight, it may become difficult to obtain an absorbent resin having high diffusing absorbency under pressure.

The surface crosslinking agent referred herein is a mixture of compounds that can react with carboxyl groups of the absorbent resin precursor, that is to say, a mixture of the first surface crosslinking agent and second surface crosslinking agent having their respective solubility parameter values (SP values). The solubility parameter value is generally used as a factor representing the polarity of a compound. The present invention adopts a solubility parameter $\delta(cal/cm^3)^{1/2}$ of solvents set forth in pages 527–539 of the Polymer Handbook, the third edition, Wiely Interscience. As to the solvents which are not found in the above pages, the solubility parameter is calculated by substituting a Hoy's condense energy constant set forth in page 525 into a Small's equation set forth in page 524.

A preferable first surface crosslinking agent is a compound capable of reacting with carboxyl groups of the absorbent resin precursor and having solubility parameter of 12.5 $(cal/cm^3)^{1/2}$ or higher, and more preferably, 13.0 $(cal/cm^3)^{1/2}$ or higher. Examples of the first surface crosslinking agent include, but are not limited to: ethylene glycol, propylene glycol, glycerin, pentaerythritol, sorbitol, ethylenecarbonate (1,3-dioxolane-2-one), propylenecarbonate(4-methyl-1,3-dioxolane-2-one), etc. One member or a mixture of two or more members selected from these first surface crosslinking agents can be used effectively.

A preferable second surface crosslinking agent is a compound capable of reacting with carboxyl groups of the absorbent resin precursor and having solubility parameter below 12.5 $(cal/cm^3)^{1/2}$, and more preferably, in a range between 9.5 $(cal/cm^3)^{1/2}$ and 12.0 $(cal/cm^3)^{1/2}$. Examples of the second crosslinking agent include, but are not limited to: diethylene glycol, triethylene glycol, tetraethylene glycol, dipropylene glycol, tripropylene glycol, 1,3-butanediol, 1,4-butanediol, 1,5-pentanediol, 2,4-pentanediol, 1,6-hexanediol, 2,5-hexanediol, trimethylolpropane, diethanolamine, triethanolamine, ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, ethylenediamine, diethylenetriamine, triethylene tetramine, 2,4-tolylene diisocyanate, hexamethylenediisocyanate, 4,5-dimethyl-1,3-dioxolane-2-one, epichlorohydrin, epibromohydrin, etc. One member or a mixture of two or more members selected from these second surface crosslinking agents can be used effectively.

An amount of use of the surface crosslinking agent varies depending on the kinds of compounds and a combination thereof; however, a preferable amount of the first surface crosslinking agent and that of the second surface crosslinking agent with respect to 100 parts by weight of solid content of the absorbent resin precursor is in a range between 0.01 part by weight and 5 parts by weight, and in a range between 0.001 part by weight and 1 part by weight, respectively, and more preferably, in a range between 0.1 part by weight and 2 parts by weight and in a range between 0.005 part by weight and 0.5 part by weight, respectively. An amount exceeding the above specified ranges is not preferable because it is excessive to enable the absorbent resin to form an optimal crosslinking structure, besides it is not economical. An amount below the above specified ranges is not preferable either, because it is not sufficient to attain appreciable improvement in the properties of the absorbent resin, such as diffusing absorbency under pressure.

It is preferable to use water as a solvent when the absorbent resin precursor and surface crosslinking agent are mixed. An amount of use of water varies depending on the kinds or particle diameter of the absorbent resin precursors; however, a preferred range with respect to 100 parts by weight of solid content of the absorbing agent precursor is between 0 part by weight exclusive and 20 parts by weight inclusive, and more preferably, between 0.5 parts by weight and 10 parts by weight.

When the absorbent resin precursor and the surface crosslinking agent are mixed, a hydrophilic organic solvent may be used optionally as a solvent. Examples of the hydrophilic organic solvent include:

lower alcohols, such as methyl alcohol, ethyl alcohol, n-propyl alcohol, isopropyl alcohol, n-butyl alcohol, isobutyl alcohol, and t-butyl alcohol;

ketons, such as acetone;

ethers, such as dioxane, tetrahydrofuran, alcoxypolyethylene glycol;

amides, such as N,N-dimethylformamide;

sulfoxides, such as dimethylsulfoxide; etc.

An amount of use of the hydrophilic organic solvent varies depending on the kinds and particle diameter of the absorbent resin precursor; however, a preferred range with respect to 100 parts by weight of solid content of the absorbing agent precursor is up to 20 parts by weight, and more preferably, between 0.1 part by weight and 10 parts by weight.

When the absorbent resin precursor and the surface crosslinking agent are mixed, the absorbent resin precursor is, for example, dispersed in any of the above example hydrophilic organic solvents, and after which the crosslinking agent is mixed. However, a method of mixing is not limited to the above. of all the possible mixing methods, the preferred is a method in which the surface crosslinking agent dissolved into water and/or hydrophilic organic solvent is mixed with the absorbent resin precursor directly or through atomization or dripping.

A preferred mixing device (hereinafter, referred to as the mixing device a) for mixing the absorbent resin precursor and the surface crosslinking agent has a mixing force large enough to mix these two elements homogeneously in a secure manner. Preferred example of the mixing device a include: a cylindrical mixer, a double wall conical mixer, a V-shaped mixer, a ribbon type mixer, a screw type mixer, a fluidized-oven rotary desk mixer, a flash type mixer, a two-arm type kneader, an internal mixer, a grinding kneader, a rotary mixer, a screw type extruder, etc.

After the absorbent resin precursor and the surface crosslinking agent are mixed, the resulting mixture is subject to heat treatment to surface crosslink the absorbent resin precursor. The temperature of the heat treatment varies depending on the kinds of the surface crosslinking agents; however, a preferable range is between 160° C. and 250° C. inclusive. The heat treatment at a temperature below 160° C. is not preferable because it is not high enough to form a uniform crosslinking structure and therefore the resulting absorbent resin does not exhibit high diffusing absorbency under pressure. besides, the heat treatment takes too long, which lowers the productivity as a result. The heat treatment at a temperature above 250° C. is not preferable either, because the absorbent resin precursor deteriorates and the resulting absorbent resin exhibits poor properties.

The heat treatment is carried out using a typical dryer or furnace. Examples of the dryer include: a channel mixing dryer, a rotary dryer, a desk dryer, a fluidized-bed dryer, a flash type dryer, an infra-red dryer, etc.

Examples of the water-insoluble inorganic powders contained in the absorbing agent composition of the present invention optionally include, but are not limited to: silicon dioxide, titanium dioxide, aluminium oxide, magnesium oxide, zinc oxide, talc, calcium phosphate, barium phosphate, silicic acid, silicate, clay, diatom earth, zeolite, bentonite, kaolin, hydrotalcite, activated clay, etc. One member or a mixture of two or more members selected from these water-insoluble inorganic powders can be used effectively. Of all these examples, microscopic noncrystal silicon dioxide is preferred. Further, a preferred particle diameter of the noncrystal silicon dioxide is 1,000 µm or smaller, and more preferably 100 µm or smaller, further preferably 50 µm or smaller, and most preferably 10 µm or smaller.

An amount of use of the water-insoluble inorganic powders varies depending on the use of the absorbing agent composition or the like; however, a preferred range with respect to 100 parts by weight of the absorbent resin is between 0.05 part by weight and 2 parts by weight, and more preferably between 0.1 part by weight and 1 part by weight. If the used amount is less than 0.05 part by weight, the resulting absorbing agent composition may not exhibit a desired diffusing absorbency index under pressure. On the other hand, using an amount exceeding 2 parts by weight does not necessarily attain appreciable effects for the increased amount, meaning that it is not economical.

Preferred examples of a mixing device (hereinafter referred to as the mixing device b) for mixing absorbent resin and water-insoluble inorganic powders include: a cylindrical mixer, a screw type mixer, a screw type extruder, a turbulizer, a nauter type mixer, a V-shaped mixer, a ribbon type mixer, a two-arm type kneader, a fluidized mixer, a flash type mixer, a rotary disk mixer, a roll mixer, a rotary mixer, etc. The mixing speed can be either high or low. Note that it is preferable to mix the water-insoluble inorganic powders and the absorbent resin without using a solvent, which is known as dry blend. However, if a solvent is used, emulsion of water-insoluble inorganic powders may be mixed with the absorbent resin.

The polyamine compound optionally contained in the absorbing agent composition of the present invention is not especially limited as long as the same has a weight average molecular weight of 5,000 or more. The polyamine compound is not especially limited, but must contain at least one kind of amino group selected from a group consisting of a primary amino group, a secondary amino group, and a tertiary amino group in one molecule.

Examples of the polyamine compound include:

(1) a homopolymer of a monoallylamine derivative and a homopolymer of a diallylamine derivative;

(2) a copolymer of more than one kind of monoallylamine derivatives, a copolymer of more than one kind of diallylamine derivatives, a copolymer of a monoallylamine derivative and a diallylamine derivative;

(3) a copolymer of a monoallylamine derivative and/or diallylamine derivative, and a dialkyldiallylammonium salt;

(4) a homopolymer of an unsaturated carboxylic acid derivative containing a tertiary amino group (hereinafter referred to as the unsaturated carboxylic acid derivative a);

(5) a copolymer of more than one kind of the unsaturated carboxylic acid derivatives a;

(6) a copolymer of the unsaturated carboxylic acid derivative a, and an unsaturated carboxylic acid derivative containing quaternary ammonium salt which is in effect a protonic and/or alkylated tertiary amino group, and/or a dialkyldiallylammonium salt as a substituent group (hereinafter referred to as the unsaturated carboxylic acid derivative b);

(7) a ternary copolymer of the unsaturated carboxylic acid derivatives a and b, and a vinyl monomer copolymerizable with the unsaturated carboxylic acid derivatives a and b;

(8) a polymer produced by copolymerizing an unsaturated carboxylic acid and an unsaturated monomer copolymerizable with the unsaturated carboxylic acid first, and thence reacting alkyleneimine with a carboxyl group of the resulting copolymer;

(9) polyalkyleneimine;

(10) a polyalkyleneimine-epihalohydrin resin;

(11) polyalkylenepolyamine;

(12) a polymer of (2-methacryloyloxyethyl) ethyleneimine, and a copolymer of (2-methacryloyloxyethyl)ethyleneimine and an unsaturated monomer copolymerizable with (2-methacryloyloxyethyl) ethyleneimine;

(13) polyamidepolyamine;

(14) polyamideamine epihalohydrin resin;

(15) denaturated polyacrylamide as a result of Mannich reaction and denaturated polymethacrylamide as a result of Mannich reaction;

(16) polyvinylamine, and a copolymer of vinylamine and an unsaturated monomer copolymerizable with vinylamine;

(17) a condensation polymer of dicyandiamide diethylenetriamine; etc.

To be more specific, examples of the polyamine compound include:

polyallylamine, polydiallylamine, poly(N-alkylallylamine), poly(alkyldiallylamine), a copolymer of monoallylamine-diallylamine, a copolymer of N-alkylallylamine-monoallylamine, a copolymer of monoallylamine-dialkyldiallylammonium salt, a copolymer of diallylamine-dialkyldiallylammonium salt, polydimethylaminoethyl acrylate, polydiethylaminoethyl acrylate, polydimethylaminoethyl acrylamide, straight-chain polyethyleneimine, branched-chain polyethyleneimine, polyethylenepolyamine, polypropylenepolyamine, polyamidepolyamine, polyetherpolyamine, polyvinylamine, polyamidepolyamine epichlorohydrin resin, polyamidine, etc. The examples also include amino denaturated products produced by reacting formaldehyde and diethylamine with polyacrylamide or polymethacrylamide.

The polyamine compound may be neutralized by an acid compound, either entirely or partially. The acid compound may be any compound capable of neutralizing the polyamine compound, that is to say, any inorganic acid and organic acid. Example of inorganic acid include:

carbonic acid;

hydroacids, such as hydrochloric acid and hydrofluoric acid;

oxygen acids, such as sulfuric acid, sulfurous acid, nitric acid, hypoposphorous acid, phosphorous acid, orthophosphoric acid, metaphosphoric acid, polyphosphoric acid including pyrophosphoric acid, tripolyphosphoric acid, ultraphosphoric acid (acid metaphosphoric acid), perchloric acid;

salts of the above oxygen acids; etc.

Examples of the organic acid include compounds containing an acid functional group, such as carboxylic acid, sulfinic acid, sulfonic acid, phenolic acid, enol (a tautomer of a carbonyl compound), mercaptan, imide (acid imide), oxime, sulfonamide, etc. To be more specific, examples of the organic acid include:

hydroxy acids, such as glycolic acid, lactic acid, trichlorolactic acid, glyceric acid, malic acid, tartaric acid, citric acid, tartronic acid, and gallic acid;

amino acids, such as aspartic acid; etc. One member or a mixture of two or more members selected from these acid compounds can be used effectively.

The polyamine compound has a weight average molecular weight of 5,000 or higher, and a preferred range of the same is between 10,000 and 10,000,000. Using a polyamine compound having a weight average molecular weight below 5,000 is not preferable, because the resulting absorbing agent composition often fails to exhibit a desired diffusing absorbency index under pressure. An amount of use of the polyamine compound varies depending on the use of the resulting absorbing agent composition; however, a preferred range with respect to 100 parts by weight of the absorbent resin is between 0.1 part by weight and 10 parts by weight.

In a suitable method of mixing the absorbent resin and polyamine compound, a solution or dispersion liquid is prepared by dissolving or dispersing the polyamine compound into water and/or any of the aforementioned hydrophilic organic solvents, and the solution or dispersion liquid is mixed with the absorbent resin through atomization or dripping. The absorbent resin and polyamine compound are mixed with each other by any of the above-mentioned mixing devices b. The mixing speed can be either high or low.

The water-insoluble inorganic powders and polyamine compound may be used separately or together. The mixing order of the absorbent resin, water-insoluble inorganic powders, and polyamine compound is not especially limited.

As previously mentioned, the absorbing agent composition of the present invention can be obtained by another method, which will be described below.

In the first place, the absorbent resin precursor is adjusted in such a manner to contain carboxyl groups, have an average particle diameter in a range between 200 μm and 600 μm, and contain up to 10 weight percent particles having a diameter smaller than 106 μm. Then, the absorbent resin precursor is subject to heat treatment under the presence of the first and second surface crosslinking agents reactive with the carboxyl group at 160° C. or higher to produce an absorbent resin: the first surface crosslinking agent has a solubility parameter of 12.5 $(cal/cm^3)^{1/2}$ or higher while the second surface crosslinking agent has a solubility parameter below 12.5 $(cal/cm^3)^{1/2}$.

In the second place, the surface crosslinking agent, preferably, the first surface crosslinking agent having a solubility parameter of 12.5 $(cal/cm)^{1/2}$ or higher and the second surface crosslinking agent having a solubility parameter below 12.5 $(cal/cm^3)^{1/2}$, is added to the resulting absorbent resin and mixed, after which the resulting mixture is subject to heat treatment at 160° C. or higher.

The non-volatile water-soluble compound optionally contained in the absorbing agent composition of the present invention has a boiling point of 150° C. or higher under normal pressure, remains in a solid state at room temperature, and at least 1 g of which dissolves into 100 g of water at room temperature. A compound that remains in a solid state at room temperature, or has a boiling point of 200° C. or higher under normal pressure is preferable. More preferable is a compound at least 10 g of which dissolves into 100 g of water at room temperature, and further preferable is a compound at least 100 g of which dissolves into 100 g of water at room temperature. When the absorbing agent composition is used in the absorbent product, such as paper diapers, using the above non-volatile water-soluble compound makes it possible to improve urine resistance while reducing an amount of wet back of an aqueous liquid (an amount of the absorbed aqueous liquid seeps back from the absorbing agent composition).

Examples of the non-volatile water-soluble compound include organic compounds containing at least one functional group selected from a group consisting of hydroxyl group, carboxyl group, amide group and amino group, and inorganic compounds exhibiting basic properties to the absorbent resin. The inorganic compounds exhibiting basic properties to the absorbent resin referred herein is a compound having a higher pH than the absorbent resin. A compound preferred as such inorganic compounds has a pH of 8.5 or higher, more preferably 9.0 or higher, and most preferably in a range between 10 and 14.

Of all the above organic compounds, those containing at least one hydroxyl group in a molecule, or namely, alcohols, are not especially limited as long as they are water soluble. Examples of the alcohols include:

monohydroxy alcohols, such as glycolic acid and methoxypolyethylene glycol;

polyhydroxy alcohols, such as ethylene glycol, propylene glycol, glycerin, polyglycerin, pentaerythritol, sorbitol, diethylene glycol, triethylene glycol, tetraethylene glycol, dipropylene glycol, tripropylene glycol, 1,3-butanediol, 1,4-butanediol, 1,5-pentanediol, 2,4-pentanediol, 1,6-hexanediol, 2,5-hexanediol, trimethylolpropane, diethanolamine, triethanolamine, polyethylene glycol, polyvinyl alcohol, a block copolymer of oxyethylene-oxypropylene, a random copolymer of oxyethylene-oxypropylene, water-soluble polysaccharides represented by water-soluble starch, glucose, fructose, and saccharose;

aminoalcohols, such as monoethanolamine; etc. of all these examples, polyhydroxy alcohols and aminoalcohols are preferred, and particularly, polyhydroxy alcohols are preferred. Using at least one alcohol selected from a group consisting of polyhydroxy alcohols and aminoalcohols makes it possible to improve urine resistance of the absorbent products using the resulting absorbing agent composition, such as paper diapers.

Among the polyhydroxy alcohols, those having at least three hydroxy groups, such as glycerin, sorbitol, and saccharose, may be modified by etherifying or esterifying a part of hydroxyl groups of these polyhydroxy alcohols, provided that one molecular contains a plurality of hydroxyl groups and these polyhydroxy alcohols remain water soluble after the modification. Examples of such modified polyhydroxy alcohols include: glycerol monofatty acid ester, polyoxyethylene fatty acid ester, saccharose fatty acid ester, etc.

These polyhydroxy alcohols or aminoalcohols may be prepared before they are mixed with the absorbent resin or the precursors of these alcohols, namely, ethyleneoxide, alkylenecarbonate or the like, may be converted to the polyhydroxy alcohols or aminoalcohls after they are mixed with the absorbent resin. When the absorbent resin is made into agglomerated particles or a sheet, the polyhydroxy alcohols may be used as a plasticizer or binder. The polyhydroxy alcohols exhibit the resulting absorbing agent composition some functions, such as plasticity and adhesive properties to a substrate made of hydrophilic fibers (which will be explained below) or the like. Moreover, besides being able to ensure high safety, the polyhydroxy alcohols can improve the mixing properties of the absorbing agent composition and hydrophilic fibers or the like in the absorbent material without causing coloring.

Of all the above organic compounds, those containing at least one carboxyl group in one molecule, namely, carboxylic acid, is not especially limited as long as they are water soluble. Preferred carboxylic acids are carboxylic acid and a salt thereof, and examples of which include:

anisate, bezonate, formate, valerate, glyoxylate, glycolate, glycerol phosphate, glutarate acid, chloroacetate, chloropropionate, cinnamate, succinate, acetate, tartrate, lactate, pyruvate, fumarate, propionate, 3-hydroxypropionate, maleate, malonate, butyrate, isobutyrate, imidinoacetate, malate, citraconate, adipate, itaconate, crotonate, salicylate, gluconate, gallate, sorbate, p-oxybezonate, etc. Of all these salts of carboxylic acid, salts of polycarboxylic acid are preferred, and salts of dicarboxylic acid are more preferred, among which maleate and malonate are particularly preferred.

Of all these organic compounds, the examples of water-soluble compounds containing at least one amide group in one molecule include urea. When the absorbent resin is made into agglomerated particles or a sheet, the urea may be used as a binder.

The inorganic compound is not especially limited as long as it is water soluble. Examples of the. inorganic compound include: ammonia, phosphate, diphosphate, tripolyphosphate, sulfate, hydrochloric acid, carbonate, hydrogen carbonate, alkali metal hydroxide, sodium carbonate, sodium hydrogencarbonate, sodium hydroxide, potassium hydroxide, etc. Of all these examples, ammonia, phosphate, carbonate, hydrogen carbonate, and alkali metal hydroxide are preferred, and carbonate and hydrogen carbonate are particularly preferred. Using carbonate or hydrogen carbonate makes it possible to improve urine resistance of the absorbent product using the resulting absorbing agent composition, such as paper diaper.

An amount of use of the non-volatile water-soluble compound varies depending on the use of the resulting absorbing agent composition; however, a preferred range is between 1 percent by weight and 50 percent by weight, more preferably between 2 percent by weight and 45 percent by weight, and most preferably between 5 percent by weight and 40 percent by weight based on the weight of the absorbent resin. Using the non-volatile water-soluble compound within the above ranges makes it possible to improve urine resistance of the absorbent product using the resulting absorbing agent composition, such as paper diaper, while reducing an amount of wet back of an aqueous liquid. Using less than 1 weight percent non-volatile water-soluble compound may make it impossible to improve the urine resistance and to reduce an amount of wet back of the aqueous liquid. Whereas using more than 50 weight percent non-volatile water-soluble compound reduces the liquid permeability or liquid diffusion, thereby making it impossible to obtain an absorbing agent composition exhibiting desired absorbing properties.

One member or a mixture of two or more members selected from these non-volatile water-soluble compounds can be used effectively. The non-volatile water-soluble compounds are either organic or inorganic compounds, or a mixture thereof. The most preferable non-volatile water-soluble compound is polyhydroxy alcohols.

When the absorbent resin and non-volatile water-soluble compound are mixed, water and/or any of the aforementioned hydrophilic organic solvents may be used optionally as a solvent. An amount of use of the solvent varies depending on the kinds and particle diameter of the absorbent resin; however, a preferred range with respect to 100 parts by weight of the absorbent resin is up to 20 parts by weight, and more preferably between 0.1 part by weight and 10 parts by weight. When the absorbent resin and non-volatile water-soluble compound are mixed using the solvent, the resulting absorbing agent composition may be dried optionally by heating or the like. A preferable heating temperature is in a range between 40° C. and 300° C., and more preferably between 50° C. and 200° C.

The absorbent resin and non-volatile water-soluble compound are mixed by any of the aforementioned mixing devices b. The mixing speed can be either high or slow. When using a solid non-volatile water-soluble compound, it is preferable to use the aforementioned solvents.

The reason why the absorbing agent composition containing the non-volatile water-soluble compound of the present invention exhibits good urine resistance is not clear. However, compounds, such as a decomposing enzyme, that play a role of a catalyst in urine-induced deterioration, are assumed to be made less active because the surface of the absorbent resin is crosslinked more uniformly and the crosslinking density is increased and the specific non-volatile water-soluble compound is added.

The reason why the absorbing agent composition containing the non-volatile water-soluble compound of the present invention can reduce an amount of wet back of an aqueous liquid even when the liquid permeability is increased is not clear either. However, the non-volatile water-soluble compound is presumed to suppress the wet back of a liquid existing in interstitial spaces among the hydrophilic fibers and among swelled gel (swelled absorbent resin).

Besides the above effect, when the non-volatile water-soluble compound is added to an absorbent resin having diffusing absorbency under pressure of 25 g/g or higher with respect to 0.9 weight percent sodium chloride solution under a load of 20 g/cm$^2$ after 60 minutes since the absorption started, not only the urine resistance of the absorbent product using the resulting absorbing agent composition, such as paper diapers, can be increased, but also an amount of wet back of the aqueous liquid can be reduced.

The absorbing agent composition obtained by any of the above methods has diffusing absorbency index under pressure of 1.5 g/g·min or higher with respect to a 0.9 weight percent sodium chloride solution under a load of 20 g/cm$^2$, thereby exhibiting excellent absorbing properties explained above.

The absorbent material of the present invention includes at least one of the aforementioned absorbing agent compositions in an amount of 40 percent by weight or higher, more preferably 50 percent by weight or higher, further preferably 60 percent by weight or higher, and most preferably 70 percent by weight or higher.

An absorbent material containing an absorbing agent composition having a diffusing absorbency index under pressure of 1.5 g/g·min or higher can readily absorb an aqueous liquid supplied in bulk, thereby making increasing an overall absorbing capacity of the absorbent material. In contrast, an absorbent material containing an absorbing agent composition having diffusing absorbency index under pressure below 1.5 g/g·min can not readily absorb an aqueous liquid supplied in bulk. In other words, the absorbent material containing such an absorbing agent composition has a low diffusing absorbency index under pressure, and therefore exhibits poor liquid diffusion. For this reason, the above absorbent material can neither readily absorb an aqueous liquid supplied in bulk nor diffuse the same inside. As a result, it takes quite a long time for the absorbent material to absorb the supplied aqueous liquid, thereby reducing an overall absorbing capacity of the absorbent material. Further, an absorbent product using the above absorbent material may cause inconveniences, such as leakage, when an aqueous liquid is supplied in bulk for the reason specified above. Such inconveniences become apparent when the aqueous liquid is repetitively supplied in bulk to the same spot of the absorbent product.

The absorbent material of the present invention may optionally contain hydrophilic fibers besides the absorbing agent composition. An absorbent material made of the absorbing agent composition and hydrophilic fibers is arranged to have the following structures in which:

the absorbing agent composition and hydrophilic fibers are mixed homogeneously;

the absorbing agent composition is sandwiched by layers of the hydrophilic fibers;

the absorbing agent composition and hydrophilic fibers are mixed homogeneously and made into a layer, and after which a layer of the hydrophilic fibers is formed thereon;

after the absorbing agent composition and hydrophilic fibers are mixed homogeneously and made into a layer to sandwich the absorbing agent composition with another layer of the hydrophilic fibers; etc. Further, the absorbent material may be the absorbing agent composition made into a sheet with a predetermined amount of water. These structures further improve the absorbing properties of the resulting absorbent material.

Among of all these structures, the preferred is the structure in which the absorbing agent composition and hydrophilic fibers are mixed homogeneously in such a manner that the absorbent material include the absorbing agent composition in an amount (ratio) of 40 percent by weight or more. The more preferred is the structure in which the absorbing agent composition and hydrophilic fibers are mixed homogeneously in such a manner that the absorbent material include at least 50 weight percent, more preferably at least 60 weight percent, and most preferably at least 70 weight percent, absorbing agent composition based on the combined weight of the absorbing agent composition and hydrophilic fibers. In the present invention, the higher the resin concentration the absorbent material has, the more significant the absorption properties appear. Note that the structure of the absorbent material is not limited to the above examples.

Examples of the hydrophilic fibers include, but are not limited to:

cellulose fibers obtained out of woods, such as mechanical pulp, chemical pulp, semi-chemical pulp, and dissolving pulp;

artificial cellulose fibers, such as rayon and acetate; etc. Of all these fibers, cellulose fibers are preferable. The hydrophilic fibers may include synthetic fibers, such as polyamide, polyester, and polyolefin.

When the absorbent material contains the hydrophilic fibers in a relatively small ratio, the absorbent material, namely, the hydrophilic fibers, may be adhered to each other using an adhesive binder. By so doing, the resulting absorbent material exhibits better strength and anti-deformation properties before or during the use.

Examples of the adhesive binder include: polyolefin fibers of thermal-fused fibers, such as polyethylene, polypropylene, a copolymer of ethylene-propylene, and a copolymer of 1-butene-ethylene; adhesive emulsion; etc. One member or a mixture of two or more members selected from these binders can be used. A preferable weight ratio of the hydrophilic fibers/adhesive binder(s) is in a range between 50/50 and 99/1, more preferably between 70/30 and 95/5, and most preferably 80/20 and 95/5.

The absorbent material thus obtained exhibits excellent absorbing properties as mentioned above.

The absorbent material of the present invention, when used in sanitary goods, such as paper diapers, sanitary napkins, and incontinence pads, can exhibit excellent properties (absorbing properties), such as high liquid diffusion and absorbency under pressure and a constant absorbing capacity over a long period, even when an amount of the absorbent resin is increased or the resin concentration is high.

The absorbent product of the present invention comprises a liquid permeable sheet and a liquid impermeable sheet sandwiching an absorbent layer containing the above absorbent material. The structure and producing method of the absorbent layer are not especially limited. The method of producing the absorbent product is not especially limited, either.

The liquid permeable sheet is made of a material capable of transmit an aqueous liquid. Examples of such a material include: non-woven fabric, woven fabric; a porous synthetic resin film made of polyethylene, polypropylene, polyester, polyamide; etc. On the other hand, the liquid impermeable sheet is made of a material incapable of transmitting an aqueous liquid. Examples of such a material include: a synthetic resin film made of polyethylene, polypropylene, ethylene vinylacetate, polyvinyl chloride; a film made of the above synthetic resins and non-woven fabric; a film made of the above synthetic resins and woven fabric; etc. Note that the liquid impermeable sheet may transmit steam.

The above-structured absorbent product exhibits the excellent absorbing properties explained above. The absorbent product includes, but is not limited to, sanitary goods, such as paper diapers, sanitary napkins, and incontinence pads. Since the absorbent product of the present invention exhibits excellent absorbing properties, the same can prevent the leakage of urine while securing a feeling of dryness, when used as a paper diaper.

The above absorbing agent composition, absorbent material, and absorbent product may optionally include deodorant, anti-bacterial agent, perfume, foaming agent, pigment, dye, hydrophilic short fiber, fertilizer, oxidizing agent, reducing agent, water, etc. to provide additional functions.

The present invention will be described in detail by way of examples and comparative examples. However, the present invention is not limited to the disclosure below. The properties (physical properties) of the absorbing agent composition, absorbent material, and absorbent product are measured in the following manner.

(a) Absorbency

Here, 0.2 g of the absorbing agent composition is uniformly placed into a bag (60 mm×60 mm) made of non-woven fabric, and allowed to remain immersed in a 0.9 weight percent sodium chloride solution (physiological saline solution) at room temperature for 60 minutes. Then, the bag is taken out, and subject to hydro-extraction for 3 minutes at 250 G using a centrifugal separator, and the weight $W_1$ (g) of the bag is measured. Further, the same processes are carried out with an empty bag, and the weight $W_0$ (g) of the empty bag is measured. The absorbency (g/g) is calculated using the weights $W_1$ and $W_0$ on the basis of the following equation:

$$\text{Absorbency (g/g)} = \frac{(\text{Weight } W_1 \text{ (g)} - \text{Weight } W_0 \text{ (g)})}{\text{Weight of Absorbing Agent Composition (g)}}$$

When the absorbing agent composition includes additives other than the absorbent resin (for example, non-volatile water-soluble compound, water-insoluble inorganic powders, polyamine compound, etc.) in the combined amount of 5 percent by weight or more, the absorbency (g/g) is calculated on the basis of the following equation:

$$\text{Absorbency (g/g)} = \frac{(\text{Weight } W_1 \text{ (g)} - \text{Weight } W_0 \text{ (g)})}{\text{Weight of Absorbent Resin (g)}}$$

where "Weight of Absorbent Resin" is a weight of the absorbent resin contained in 0.2 g of the absorbing agent composition.

(b) Diffusing Absorbency under Pressure

To begin with, a device measuring the diffusing absorbency under pressure of the absorbing agent composition will be briefly explained below with reference to FIGS. 1 and 2.

As shown in FIG. 1, the measuring device includes a balance 1, a container 2 of a predetermined capacity placed on the balance 1, an air-intake pipe 3, a conduit 4, a glass filter 6, and a measuring section 5 placed on the glass filter 6. The container 2 has an opening 2a on the top and an opening 2b on the side, and the air-intake pipe 3 is inserted through the opening 2a while the conduit 4 is fixed to the opening 2b. Further, a predetermined amount of physiological saline solution 12 is poured in the container 2. The lower end portion of the air-intake pipe 3 is dipped into the physiological saline solution 12. The glass filter 6 has a diameter of 70 mm. The container 2 and the glass filter 6 communicate with each other through the conduit 4. The glass filter 6 is fixed in such a manner that the upper surface of the same is positioned slightly above the lower end of the air-intake pipe 3.

Figure 2:
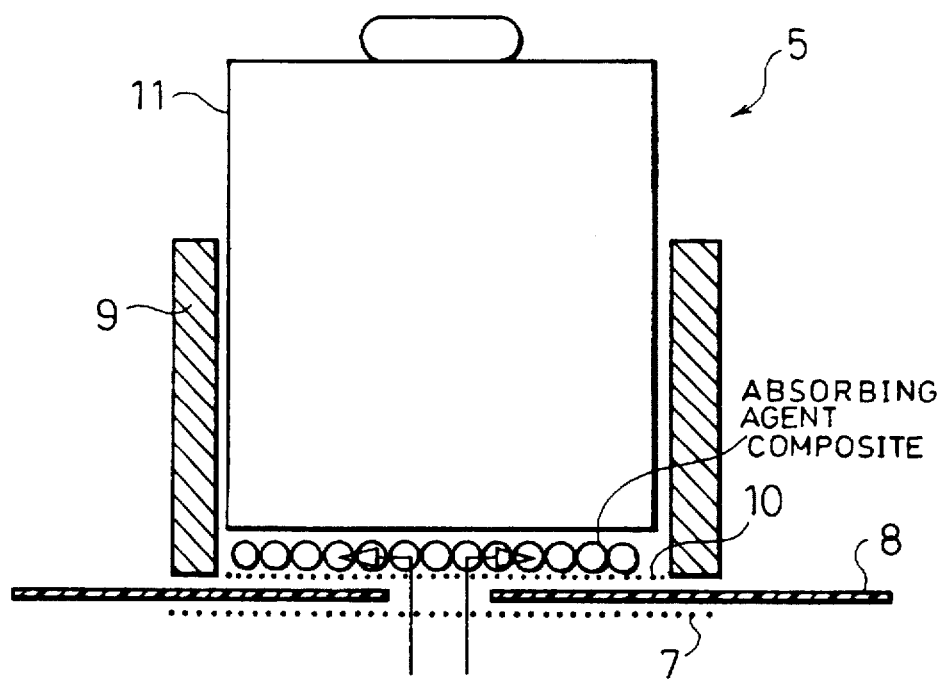
FIG. 2 is a cross section showing a major portion of the above measuring device.

As shown in FIG. 2, the measuring section 5 is provided with a paper filter 7, a sheet 8, a supporting cylinder 9, a metal gauze 10 affixed to the bottom of the supporting cylinder 9, and a weight 11. In the measuring section 5, the paper filter 7, sheet 8, and supporting cylinder 9 (that is, the metal gauze 10) are sequentially placed on the glass filter 6 in this order, and the weight 11 is placed on the metal gauze 10 inside the supporting cylinder 9. The sheet 8 is a 0.1 mm-thick toroidal made of polyethylene terephthalate (PET) having an 18-mm-dia opening at the center. The supporting cylinder 9 has an inner diameter of 60 mm. The metal gauze 10 is made of stainless steel to have a 400-mesh (the size of each mesh: 38 μm) according to the JIS standard. A predetermined amount of the absorbing agent composition is uniformly scattered on the metal gauze 10. The weight 11 is adjusted in such a manner to apply a load of 20 g/cm$^2$ evenly to the metal gauze 10, that is, the absorbing agent composition.

The diffusing absorbency under pressure of the absorbing agent composition is measured by using the above-arranged measuring device in the manner described below.

To begin with, preparatory operations are carried out, that is predetermined amount of physiological saline solution 12 is poured into the container 2, and the air-intake pipe 3 is inserted into the container 2. Then, the paper filter 7 is placed onto the glass filter 6, and the sheet 8 is placed atop of the paper filter 7 in such a manner that its opening is superimposed on the center of the glass filter 6. At the same time, 1.5 g of the absorbing agent composition is uniformly scattered on the metal gauze 10 inside the supporting cylinder 9, and the weight 11 is placed on the absorbing agent composition.

Subsequently, the metal gauze 10, that is, the supporting cylinder 9 having the absorbing agent composition and the weight 11 inside, is placed on the sheet 8 in such a manner that the center of the supporting cylinder 9 is superimposed on the center of the glass filter 6.

Figure 3:
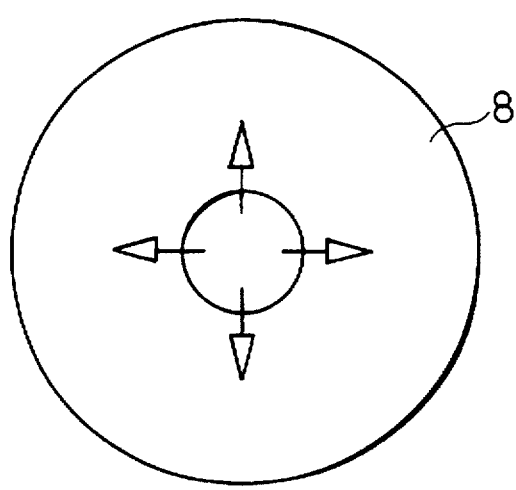
FIG. 3 is a view explaining a diffusing direction of a physiological saline solution in the above measuring device.

Then, the weight $W_2$ (g) of the physiological saline solution 12, which has been absorbed by the absorbing agent composition for 60 minutes since the supporting cylinder 9 was placed on the sheet 8, is measured by the balance 1. As shown in FIGS. 2 and 3, after passing through the opening of the sheet 8, the physiological saline solution 12 is absorbed by the absorbing agent composition while being diffused almost uniformly in the lateral direction (indicated by an arrow).

The diffusing absorbency under pressure (g/g) of the absorbing agent composition after 60 minutes since the absorption started is calculated on the basis of the following equation:

$$\text{Diffusing Absorbency under Pressure (g/g)} = \frac{\text{Weight } W_2 \text{ (g)}}{\text{Weight of Absorbing Agent Composition (g)}}.$$

When the absorbing agent composition includes additives other than the absorbent resin (for example, non-volatile water-soluble compound, water-insoluble inorganic powders, polyamine compound, etc.) in the combined amount of 5 percent by weight or more, the diffusing absorbency under pressure (g/g) is calculated on the basis with the following equation:

$$\text{Diffusing Absorbency under Pressure (g/g)} = \frac{\text{Weight } W_2 \text{ (g)}}{\text{Weight of Absorbent Resin (g)}}$$

where "Weight of Absorbent Resin" is a weight of the absorbent resin contained in 1.5 g of the absorbing agent composition.

(c) Diffusing Absorbency Index under Pressure

The diffusing absorbency index under pressure is measured using the same device used for measuring the diffusing absorbency under pressure. To be more specific, the weight of the physiological saline solution 12 absorbed by the absorbing agent composition after 60 minutes since the supporting cylinder 9 was placed on the sheet 8 is measured in time series using the balance 1. That is to say, the weight of the absorbed physiological saline solution 12 is measured per minute, preferably per second, using the balance 1. Then, the maximum absorbing capacity per unit time is calculated using the result of the above measurement, and defined as the diffusing absorbency index under pressure (g/g·min).

(d) Urine Resistance and Water-Soluble Content

To begin with, sampling urine of the same amount is collected from 10 males in a healthy condition. Then, 2 g of the absorbing agent composition is placed in a lidded glass bottle of 100 ml and the sampling urine is poured to let the absorbing agent composition swell by 25 times. Subsequently, the glass bottle containing the swelled gel is let stand for 16 hours at 37° C. in atmosphere of relative humidity of 90%.

Then, the fluidity of the swelled gel is observed visually and evaluated in four stages: "no fluidity", "no substantial fluidity", "slight fluidity", and "fair fluidity".

Further, the water-soluble content in the swelled gel is measured in the following manner. Some of the swelled gel having solid content (solid content of the absorbent resin) of 0.5 g is taken out, and dispersed in an ion exchange water of 1 and the resulting dispersion liquid is subject to stirring for 1 hour to let the gel fully swell. The dispersion liquid is filtered through a paper filter, and the filtrate is subject to titration in a predetermined manner. An amount of a compound dissolved in the filtrate produced as a result of deterioration by urine, namely, water-soluble polyacrylate and/or polyacrylic acid, is calculated based on the titre or the like, and defined as the water-soluble content (percent by weight). It is understood herein that the more the water-soluble content, the more the absorbing agent composition has been deteriorated by urine.

(e) Amount of Wet Back

Five pieces of 90-mm-dia filters (Advantech Toyo Kabushiki Kaisha, Model No. 2) are layered. Then, the supporting cylinder 9 containing the absorbing agent composition swelled by the physiological saline solution, together with the weight 11, is removed from the measuring device used in measuring the diffusing absorbency under pressure, and the same are placed on the 5-fold filters. A weight is added to apply a load of 100 g/cm² to the absorbing agent composition uniformly. Then, an amount of physiological saline solution oozed to the 5-fold filter after 1 minute since the load of 100 g/cm² was applied is measured, and defined as an amount (g) of wet back.

(f) Diffusing absorbency under Pressure of Absorbent Material

To begin with, a device for measuring the diffusing absorbency of the absorbent material will be described with reference to FIGS. 4 and 5. Hereinafter, like components are labeled with like reference numerals with respect to the counterpart used in measuring the diffusing absorbency under pressure of the absorbing agent composition, and the description of these components is not repeated for the explanation's convenience.

Figure 4:
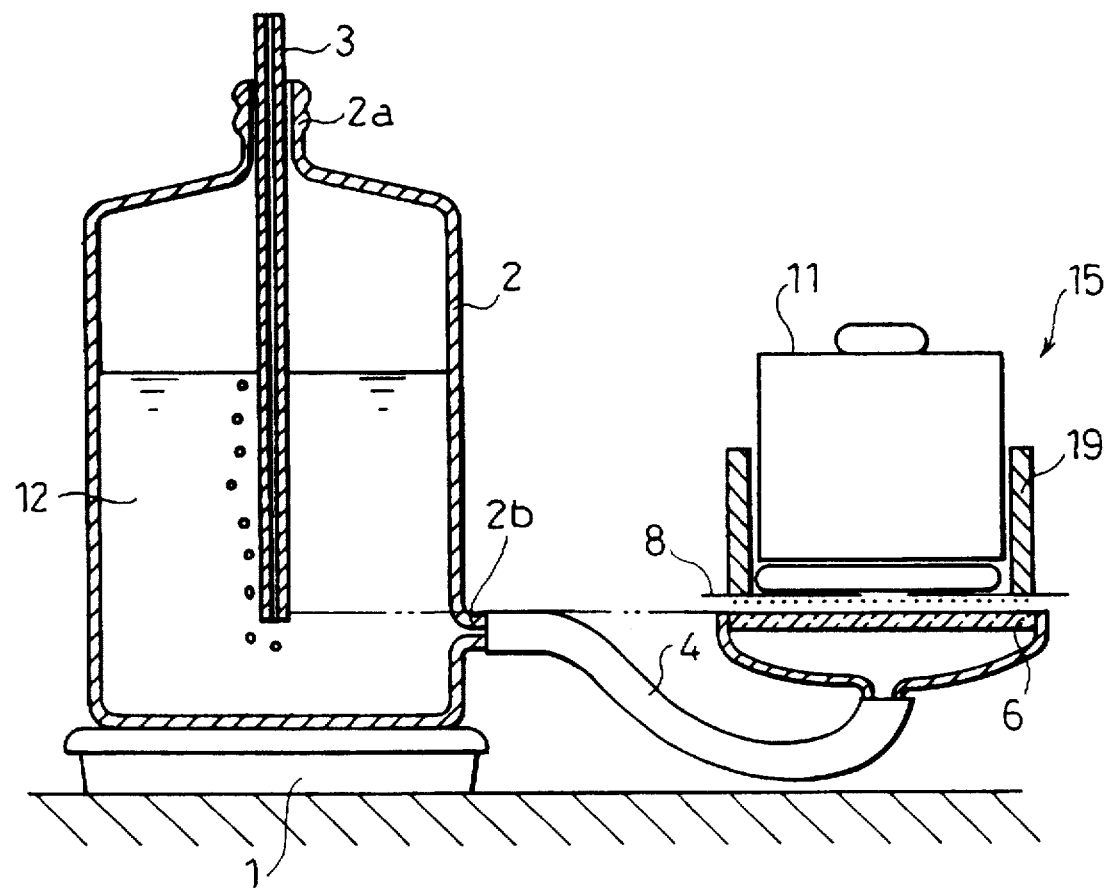
FIG. 4 is a schematic cross section of a device measuring diffusing absorbency under pressure indicating one of the properties of an absorbent material of the present invention.
Figure 5:
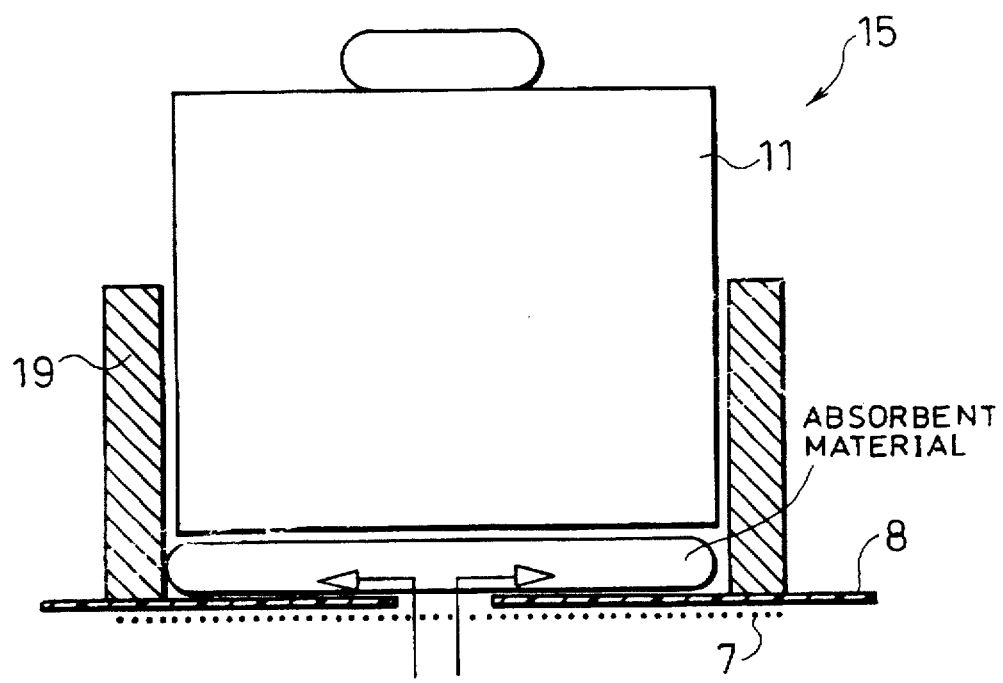
FIG. 5 is a cross section showing a major portion of the measuring device of FIG. 4.

As shown in FIG. 4, the measuring device includes a balance 1, a container 2, an air-intake pipe 3, a conduit 4, a 120-mm-dia glass filter 6, and a measuring section 15 place on the glass filter 6. As shown in FIG. 5, the measuring section 15 is provided with a paper filter 7, a sheet 8, a supporting rectangular tube 19, and a weight 11. Note that the measuring section 15 does not include the metal gauze.

In the measuring section 15, the paper filter 7, the sheet 8, and the supporting rectangular tube 19 are sequentially placed on the glass filter 6 in this order, and the weight 11 is placed inside the supporting rectangular tube 19. The sheet 8 is a 0.1 mm-thick rectangle made of polyethylene terephthalate (PET) having a 12.5 mm×100 mm opening at the center. The supporting rectangular tube 19 has an inner dimension of 100 mm×100 mm, so that an absorbent material of a predetermined size is placed inside. The rest is identical with the structure of the counterpart used to measure the diffusing absorbency under pressure of the absorbing agent composition.

The diffusing absorbency under pressure of the absorbent material is measured using the above-structured measuring device in the manner described below. To begin with, 50 parts by weight of the absorbing agent composition and 50 parts by weight of comminuted wood pulp serving as the hydrophilic fibers are mixed using a mixer through dry blending. The resulting mixture is made into a 100 mm×100 mm web, and the web is pressed under a load of 2 kg/cm² for 1 minute. As a result, an absorbent material having a basis weight of approximately 0.047 g/cm² is obtained.

Prior to the measuring, the measuring device is prepared in a predetermined manner. Then, the filter 7 is placed on the glass filter 6, and the sheet 8 is placed on the filter 7 in such a manner that the opening of the same is superimposed on the center of the glass filter 6. Then, the supporting rectangular tube 19 is placed on the sheet 8 in such a manner that the center of the same is superimposed on the center of the glass filter 6.

Subsequently, the absorbent material is placed on the sheet 8 inside the supporting rectangular tube 19, upon which the weight 11 is placed. The absorbent material and weight 11 are placed swiftly.

Figure 6:
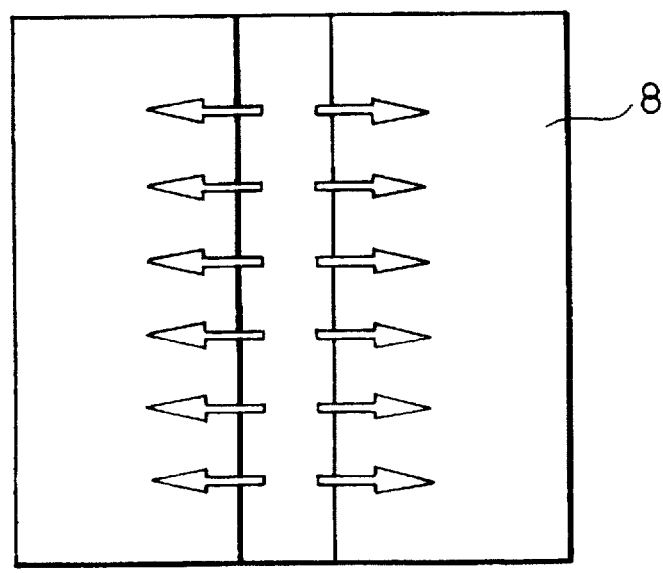
FIG. 6 is a view explaining a diffusing direction of a physiological saline solution in the measuring device of FIG. 4.

Then, a weight $W_3$ (g) of the physiological saline solution 12 absorbed in the absorbent material for 60 minutes since the absorbent material was placed on the sheet 8 is measured using the balance 1. Note that, as shown in FIGS. 5 and 6, the physiological saline solution 12 having passed through the opening of the sheet 8 is absorbed by the absorbent material while being diffused almost uniformly in the lateral direction (indicated by an arrow).

Then, the diffusing absorbency under pressure (g/g) of the absorbent material after 60 minutes since the absorption started is calculated using the weight $W_3$ on the basis with the following equation:

$$\text{Diffusing Absorbency under Pressure (g/g) of Absorbent Material} = \frac{\text{Weight } W_3 \text{ (g)}}{\text{Weight of Absorbent Material (g)}}$$

(g) Absorbing Rate under Pressure of Absorbent Material (Core Acquisition)

The absorbent material subject to measurement is produced in the following manner. To begin with, 8.8 g of the absorbing agent composition and 8.8 g of comminuted wood pulp are mixed using a mixer through dry blending. Then, the resulting mixture is made into a 260 mm×150 mm web, or the absorbent material.

On the other hand, synthetic urine is prepared by producing a water solution containing 1.9 weight percent urea, 0.8 weight percent NaCl, 0.1 weight percent $CaCl_2$, 0.1 weight percent $MgSO_4$.

Then, a load of 18 g/cm² is applied on the entire absorbent material uniformly, and a 30 mm-dia cylinder of 120 mm high is pressed against the absorbent material around the center to place the cylinder perpendicular to the absorbent material. Then, 50 g of the synthetic urine kept at 25° C. is poured into the cylinder quickly (at one time). Then, the time since the synthetic urine is poured until the same is absorbed into the absorbent material completely is measured as the first absorbing rate under pressure (sec.) The same process is repeated twice using the same absorbent material with 50-minute interval to measure the second and third absorbing rates under pressure (sec). It is understood herein that the larger the absorbency under pressure, the better the liquid diffusion of the absorbent material.

(h) Properties of Absorbent Product (using Kewpie Doll®)

The absorbent product subject to measurement is produced in the following manner. To begin with, 50 parts by weight of the absorbing agent composition and 50 parts by weight of comminuted wood pulp are mixed using a mixer through dry blending. Then, the resulting mixture is made into a 120 mm×400 mm web on a wire screen of 400-mesh (the size of each mesh: 38 µm) by a batch-type pneumatic molding device by pneumatic molding. Further, the web is pressed for 5 seconds under a load of 2 kg/cm², and as a result, an absorbent material having a basis weight of approximately 0.047 g/cm² is obtained.

Subsequently, a back sheet (liquid impermeable sheet) having a leg gather made of impermeable polypropylene, the above absorbent material, a top sheet (liquid permeable sheet) made of permeable polypropylene are laminated to each other in this order using a both-sided tape. Then, two tape fasteners are attached to the resulting lamination to obtain an absorbent product (i.e., paper diaper).

The above absorbent product is put on a Kewpie Doll® (55 cm tall and 5 kg in weight), and laid with its face downward. Then, a tube is inserted between the absorbent product and doll in such a manner that a physiological saline solution will be supplied around the same spot where a baby would discharge urine. Here, 50 ml of the physiological saline solution is repetitively supplied every 20 minutes until the absorbent product can no longer absorb the physiological saline solution and the excessive physiological saline solution starts to leak, and an amount of the physiological saline solution supplied up to this point is measured.

The above test is repeated four times and an average amount is calculated, which is defined as an absorbing capacity (g). It is understood herein that the larger the absorbed capacity, the better the properties of the absorbent product.

(EXAMPLE 1)

A reactant solution is prepared by dissolving 3.59 g of trimethylolpropane triacrylate serving as an internal crosslinking agent into 5,500 g of a water solution of 39 weight percent sodium acrylic acid (hydrophilic unsaturated monomer) neutralized by 75 percent by mole. Then, the reactant solution is subject to deaeration for 30 minutes in nitrogen gas atmosphere. Then, the reactant solution is poured into a reactor, which is a stainless lidded two-arm type kneader of 10 l with two sigma blades and a jacket. Then, the reactant system is displaced by introducing nitrogen gas while keeping the reactant solution at 30° C.

Next, 2.4 g of ammonium persulfate and 0.12 g of L-ascorbic acid serving as a polymerization initiator are added to the reactant solution with stirring. Then, the polymerization starts 1 minute later. The polymerization is proceeded at 30° C.–80° C. until 60 minutes have passed since the polymerization started, and the resulting hydrous gel of polymer is taken out.

The hydrous gel of polymer is finely divided and each particle has a diameter of approximately 5 mm. The finely divided hydrous gel of polymer is spread across the 50-mesh metal gauze and subject to hot air drying for 90 minutes at 150° C. Then, the dried gel is pulverized by a vibrating mill, and sieved to a particular diameter size using a 20-mesh metal gauze. As a result, an absorbent resin precursor of an undefined shape having an average particle diameter of 400 µm and containing 5 weight percent particles having a diameter smaller than 106 µm is obtained.

Then, a surface crosslinking agent solution, made of 0.5 part by weight of ethylene glycol (SP value: σ=14.6 (cal/cm³)$^{1/2}$) serving as the first surface crosslinking agent, 0.1 part by weight of glycerol polyglycidyl ether (SP value: σ=10.8 (cal/cm³)$^{1/2}$) serving as the second surface crosslinking agent, 3 parts by weight of water, and 1 part by weight of ethyl alcohol, is mixed with 100 parts by weight of the above absorbent resin precursor. The resulting mixture is subject to heat treatment for 40 minutes at 195° C. to obtain an absorbent resin. The average particle diameter of the resulting absorbent resin is 400 µm and it contains 3 weight percent particles having a diameter smaller than 106 µm.

Finally, the absorbing agent composition of the present invention is obtained by adding 0.5 g of microscopic powders of hydrophilic silicon dioxide (Aerosil 200 of the Nippon Aerosil Co., Ltd.) serving as water-insoluble inorganic powders to 100 g of the above absorbent resin and mixing the same.

The properties of the absorbing agent composition and the absorbent material and absorbent product using the absorbing agent composition are measured in the manner explained above. Then, the absorbing agent composition has absorbency of 30 g/g, diffusing absorbency under pressure of 26.9 g/g, and diffusing absorbency index under pressure of 2.87 g/g·min. The absorbent material has diffusing absorbency under pressure of 18.9 g/g and the first through third absorbing rate under pressure of 34 sec., 69 sec., and 77 sec., respectively. The absorbent product has an absorbing capacity of 275 g. These values indicate that each element exhibits excellent properties. The result of the measurement is set forth in TABLE 1 below.

(EXAMPLE 2)

Herein, 5 g of a water solution of 30 weight percent polyethyleneimine having a weight average molecular weight of 70,000 (Epomine P-1000 of Nippon Shokubai Co., Ltd.) serving as the polyamine compound is added to 100 g of the absorbent resin obtained in Example 1 and mixed. The resulting mixture is placed in a hot air dryer kept at 90° C. for 20 minutes to be set. The resulting set material is sieved to a particular diameter size using a mesh metal gauze (the size of each mesh: 840 μm), and 0.3 g of microscopic powders of hydrophilic silicon dioxide (Carplex 22S of Shionogi & Co., Ltd.) serving as water-insoluble inorganic powders is added to the set material having passed through the metal gauze and mixed. As a result, the absorbing agent composition of the present invention is obtained.

The properties of the absorbing agent composition, and the absorbent material and absorbent product using the absorbing agent composition are measured in the manner explained above, and the result of which is set forth in TABLE 1 below.

(EXAMPLE 3)

A reactant solution is prepared by dissolving 2.35 g of N,N'-methylenebisacrylamide serving as the internal crosslinking agent into 5,500 g of 20 weight percent acrylic acid water solution. Then, the reactant solution is subject to deaeration for 30 minutes in nitrogen gas atmosphere. Then, the reactant solution is poured into a reactor identical with the one used in Example 1, and the reactant system is displaced by introducing nitrogen gas while keeping the reactant solution at 30° C.

Next, 1.5 g of ammonium persulfate and 0.07 g of L-ascorbic acid are added to the reactant solution with stirring. Then, the polymerization starts about 1 minute later. The polymerization is proceeded at 30° C.–80° C. and 606.7 g of sodium carbonate serving as a neutralizer is added with stirring after 60 minutes since the polymerization started, and after which the polymerization is stopped and the resulting hydrous gel of polymer is taken out.

The hydrous gel of polymer is neutralized 75 percent by mole and finely divided so that each particle has a diameter of approximately 5 mm. The finely divided hydrous gel of polymer is spread across the 50-mesh metal gauze and subject to hot air drying for 90 minutes at 150° C. Then, the dried gel is pulverized by a vibrating mill, and sieved to a particular diameter size using a 20-mesh metal gauze. As a result, an absorbent resin precursor of an undefined shape having an average particle diameter of 390 μm and containing 4 weight percent particles having a diameter smaller than 106 μm is obtained.

Then, a surface crosslinking agent solution, made of 0.75 part by weight of propylene glycol (SP value: σ=12.6 (cal/cm³)$^{1/2}$) serving as the first surface crosslinking agent, 0.05 part by weight of propylene glycol diglycidyl ether (SP value: σ=10.1 (cal/cm³)$^{1/2}$) serving as the second surface crosslinking agent, 3 parts by weight of water, and 0.75 part by weight of ethylalcohol, is mixed with 100 parts by weight of the above absorbent resin precursor. The resulting mixture is heated for 40 minutes at 195° C. to obtain an absorbent resin. The average particle diameter of the resulting absorbent resin is 390 μm and it contains 3 weight percent particles having a diameter smaller than 106 μm.

Finally, the absorbing agent composition of the present invention is obtained by adding 0.3 g of microscopic powders of hydrophilic silicon dioxide (Leorosil QS-20 of Tokuyama Kabushiki Kaisha formerly known as Tokuyamasoda Kabushiki Kaisha) serving as the water-insoluble inorganic powders to 100 g of the above absorbent resin and mixing the same.

The properties of the absorbing agent composition, and the absorbent material and absorbent product using the absorbing agent composition are measured in the manner explained above, and the result of which is set forth in TABLE 1 below.

(EXAMPLE 4)

Herein, 5 g of a water solution of 30 weight percent polyethyleneimine having a weight average molecular weight of 70,000 (Epomine P-1000 of Nippon Shokubai Co., Ltd.) is added to 100 g of the absorbent resin obtained in Example 1 and mixed. Then, the resulting mixture is placed in a hot air dryer kept at 90° C. for 20 minutes to be set. The resulting set material is sieved to a particular diameter size using a metal gauze (the size of each mesh: 840 μm), and those having passed through the metal gauze are obtained as the absorbing agent composition of the present invention.

The properties of the absorbing agent composition, and the absorbent material and absorbent product using the absorbing agent composition are measured in the manner explained above, and the result of which is set forth in TABLE 1 below.

(EXAMPLE 5)

A reactant solution is prepared by dissolving 18.49 g of polyethylene glycol diacrylate (whose polyethylene glycol portion is made of an adduct of ethyleneoxide of 8 moles in average) serving as the internal crosslinking agent into 5,500 g of a water solution of 30 weight percent sodium acrylic acid neutralized 65 percent by mole. The resulting reactant solution is subject to deaeration for 30 minutes in nitrogen gas atmosphere. Then, the reactant solution is poured into a reactor identical with the one used in Example 1, and the reactant system is displaced by introducing nitrogen gas while keeping the reactant solution at 30° C.

Next, 2.3 g of ammonium persulfate and 0.12 g of L-ascorbic acid are added to the reactant solution with stirring. Then, the polymerization starts about 1 minute later. The polymerization is proceeded at 30° C.–80° C. until 60 minutes have passed since the polymerization started, and the resulting hydrous gel of polymer is taken out.

The hydrous gel of polymer is finely divided and each particle has a diameter of approximately 5 mm. The finely divided hydrous gel of polymer is spread across the 50-mesh metal gauze and subject to hot air drying for 90 minutes at 150° C. Then, the dried gel is pulverized by a vibrating mill, and sieved to a particular diameter size using a 20-mesh metal gauze. As a result, an absorbent resin precursor of an undefined shape having an average particle diameter of 360 µm and containing 5 weight percent particles having a diameter smaller than 106 µm is obtained.

Then, a surface crosslinking agent solution, made of 0.5 part by weight of glycerin (SP value: $\sigma = 16.5$ $(cal/cm^3)^{1/2}$) serving as the first surface crosslinking agent, 0.05 part by weight of ethylene glycol diglycidyl ether (SP value: 994 =10.2 $(cal/cm^3)^{1/2}$) serving as the second surface crosslinking agent, 3 parts by weight of water, and 1 part by weight of ethylalcohol, is mixed with 100 parts by weight of the above absorbent resin precursor. The resulting mixture is subject to heat treatment for 30 minutes at 195° C. to obtain an absorbent resin. The average particle diameter of the resulting absorbent resin is 360 µm and it contains 5 weight percent particles having a diameter smaller than 106 µm.

Finally, a surface crosslinking agent solution made of 0.5 part by weight of glycerin serving as the first crosslinking agent, 0.05 part by weight of ethylene glycol diglycidyl ether serving as the second surface crosslinking agent, 3 parts by weight of water, and 1 part by weight of ethyl alcohol is mixed with 100 parts by weight of the above absorbent resin. The resulting mixture is subject to heat treatment for 30 minutes at 195° C. As a result, an absorbent resin having undergone the surface crosslinking twice is obtained.

The resulting absorbent resin is used as the absorbing agent composition of the present invention and the properties of the same, and the absorbent material and absorbent product using the absorbing agent composition are measured in the manner explained above, and the result of which is set forth in TABLE 1 below.

(EXAMPLE 6)

Herein, 100 mg (5 percent by weight based on the weight of the absorbent resin) of glycerin serving as the non-volatile water-soluble compound and 10 mg (0.5 percent by weight based on the weight of the absorbent resin) of microscopic powders of hydrophilic silicon dioxide (Aerosil 200 of the Nippon Aerosil Co., Ltd.) are added to 2 g of the absorbent resin obtained in Example 3 and mixed. As a result, the absorbing agent composition of the present invention is obtained.

The properties of the absorbing agent composition, and the absorbent material and absorbent product using the absorbing agent composition are measured in the manner explained above, and the result of which is set forth in TABLE 1 below. Note that the absorbency and diffusing absorbency under pressure of the absorbing agent composition are calculated based on the weight of the absorbent resin contained in the absorbing agent composition.

Also, the urine resistance of the absorbing agent composition is evaluated as "no fluidity", and the water-soluble content and an amount of wet back of the same are 20.1 percent by weight and 2.3 g, respectively.

(Comparative Example 1)

The absorbent resin obtained in Example 1 is used as a comparative absorbing agent composition herein. The properties of the comparative absorbing agent composition, and the comparative absorbent material and absorbent product using the comparative absorbing agent composition are measured in the manner explained above, and the result of which is set forth in TABLE 1 below.

(Comparative Example 2)

The absorbent resin obtained in Example 3 is used as a comparative absorbing agent composition herein. The properties of the comparative absorbing agent composition, and the comparative absorbent material and absorbent product using the comparative absorbing agent composition are measured in the manner explained above, and the result of which is set forth in TABLE 1 below.

Also, the urine resistance of the comparative absorbing agent composition is evaluated as "light fluidity", and the water-soluble content and an amount of wet back of the same are 24.5 percent by weight and 2.8 g, respectively.

(Comparative Example 3)

A reactant solution is prepared by dissolving 7.18 g of trimethylolpropane triacrylate into 5,500 g of a water solution of 39 weight percent sodium acrylic acid neutralized 75 percent by mole. The resulting reactant solution is subject to deaeration for 30 minutes in nitrogen gas atmosphere. Then, the reactant solution is poured into a reactor identical with the one used in Example 1, and the reactant system is displaced by introducing nitrogen gas while keeping the reactant solution at 30° C.

Next, 5.0 g of sodium persulfate and 0.25 g of L-ascorbic acid are added to the reactant solution with stirring. Then, the polymerization starts about 1 minute later. The polymerization is proceeded at 30° C.–80° C. until 60 minutes have passed since the polymerization started, and the resulting hydrous gel of polymer is taken out.

The hydrous gel of polymer is finely divided and each particle has a diameter of approximately 5 mm. The finely divided hydrous gel of polymer is spread across the 50-mesh metal gauze and subject to hot air drying for 90 minutes at 150° C. Then, the dried gel is pulverized by a vibrating mill, and sieved to a particular diameter size using a 20-mesh metal gauze. As a result, an absorbent resin of an undefined shape having an average particle diameter of 360 µm and containing 5 weight percent particles having a diameter smaller than 106 82 m is obtained.

The resulting absorbent resin is used as a comparative absorbing agent composition herein. The properties of the comparative absorbing agent composition, and the comparative absorbent material and absorbent product using the comparative absorbing agent composition are measured in the manner explained above, and the result of which is set forth in TABLE 1 below.

(Comparative Example 4)

A reactant solution is prepared by dissolving 3.59 g of trimethylolpropane triacrylate into 5,500 g of a water solution of 39 weight percent sodium acrylic acid neutralized 75 percent by mole. The resulting reactant solution is subject to deaeration for 30 minutes in nitrogen gas atmosphere. Then, the reactant solution is poured into a reactor identical with the one used in Example 1, and the reactant system is displaced by introducing nitrogen gas while keeping the reactant solution at 30° C.

Next, 2.4 g of ammonium persulfate and 0.12 g of L-ascorbic acid are added to the reactant solution with stirring. Then, the polymerization starts about 1 minute later. The polymerization is proceeded at 30° C.–80° C. until 60 minutes have passed since the polymerization started, and the resulting hydrous gel of polymer is taken out.

The hydrous gel of polymer is finely divided and each particle has a diameter of approximately 5 mm. The finely divided hydrous gel of polymer is spread across the 50-mesh metal gauze and subject to hot air drying for 90 minutes at 150° C. Then, the dried gel is pulverized by a vibrating mill, and sieved to a particular diameter size using a 20-mesh metal gauze. As a result, an absorbent resin precursor of an undefined shape having an average particle diameter of 400 μm and containing 5 weight percent particles having a diameter smaller than 106 μm is obtained.

Then, a surface crosslinking agent solution, made of 0.5 part by weight of ethylene glycol, 3 parts by weight of water, and 1 part by weight of ethyl alcohol, is mixed with 100 parts by weight of the above absorbent resin precursor. The resulting mixture is subject to heat treatment for 20 minutes at 195° C. to obtain an absorbent resin. The average particle diameter of the resulting absorbent resin is 400 μm and it contains 3 weight percent particles having a diameter smaller than 106 μm.

The resulting absorbent resin is used as a comparative absorbing agent composition herein. The properties of the comparative absorbing agent composition, and the comparative absorbent material and absorbent product using the comparative absorbing agent composition are measured in the manner explained above, and the result of which is set forth in TABLE 1 below.

(Comparative Example 5)

Herein, 0.3 g of microscopic powders of hydrophilic silicon dioxide (Aerosil 200 of Nippon Aerosil Co., Ltd.) are added to 100 g of the absorbent resin obtained in Comparative Example 3 and mixed to obtain a comparative absorbing agent composition.

The properties of the comparative absorbing agent composition, and the comparative absorbent material and absorbent product using the comparative absorbing agent composition are measured in the manner explained above, and the result of which is set forth in TABLE 1 below.

(Comparative Example 6)

Herein 0.5 g of microscopic powders of hydrophilic silicon dioxide (Leorosil QS-20 of Tokuyamasoda Kabushiki Kaisha) are added to 100 g of the absorbent resin obtained in Comparative Example 4 and mixed to obtain a comparative absorbing agent composition.

The properties of the comparative absorbing agent composition, and the comparative absorbent material and absorbent product using the comparative absorbing agent composition are measured in the manner explained above, and the result of which is set forth in TABLE 1 below.

| EXAMPLE/ COMPARATIVE EXAMPLE | ABSORBING AGENT Composition | | | ABSORBENT MATERIAL | | | | |
|---|---|---|---|---|---|---|---|---|
| | ABSORBENCY (g/g) | DIFFUSING ABSORBENCY UNDER PRESSURE (g/g) | DIFFUSING ABSORBENCY INDEX UNDER PRESSURE (g/g min) | DIFFUSING ABSORBENCY UNDER PRESSURE (g/g) | ABSORBING RATE UNDER PRESSURE (Sec.) | | | ABSORBENT PRODUCT ABSORBING CAPACITY (g) |
| | | | | | 1ST | 2ND | 3RD | |
| 1 | 30 | 26.9 | 2.87 | 18.9 | 34 | 69 | 77 | 275 |
| 2 | 29 | 27.0 | 3.33 | 18.9 | 35 | 52 | 62 | 300 |
| 3 | 37 | 27.0 | 1.67 | 18.9 | 35 | 72 | 85 | 275 |
| 4 | 29 | 27.6 | 1.93 | 19.1 | 35 | 70 | 83 | 275 |
| 5 | 29 | 24.4 | 4.00 | 18.4 | 34 | 48 | 60 | 300 |
| 6 | 36 | 28.2 | 2.83 | 18.8 | 35 | 66 | 78 | 275 |
| 1 | 30 | 30.1 | 1.20 | 19.7 | 39 | 102 | 153 | 250 |
| 2 | 38 | 33.9 | 0.90 | 20.6 | 38 | 114 | 158 | 250 |
| 3 | 31 | 11.7 | 0.20 | 15.1 | 38 | 133 | 173 | 225 |
| 4 | 31 | 14.7 | 0.87 | 15.9 | 37 | 98 | 150 | 225 |
| 5 | 31 | 13.4 | 0.20 | 15.5 | 39 | 121 | 162 | 225 |
| 6 | 31 | 22.0 | 1.27 | 17.7 | 39 | 103 | 114 | 250 |

TABLE 1 reveals that the absorbing agent compositions of the present invention excel those of the comparative examples in diffusing absorbency index under pressure. Also, the absorbent materials of the present invention excel those of the comparative examples in absorbing rate under pressure and liquid diffusion. Further, the absorbent products of the present invention excel those of the comparative examples in absorbing capacity. Thus, the absorbing agent composition, absorbent material, and absorbent product of the present invention can readily absorb an aqueous liquid supplied in bulk, while exhibiting excellent properties (absorbing properties), such as capabilities of maintaining high liquid diffusion and a constant absorbing capacity per unit weight.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbing agent composition having a diffusing absorbency index under pressure of 1.5 g/g·min or higher with respect to a 0.9 weight percent sodium chloride solution under a load of 20 g/cm$^2$.

2. The absorbing agent composition as defined in claim 1 having a diffusing absorbency index under pressure of 3.0 g/g·min or higher.

3. The absorbing agent composition as defined in claim 1, wherein said absorbing agent composition has diffusing absorbency under pressure of 25 g/g or higher with respect to the 0.9 weight percent sodium chloride solution under a load of 20 g/cm² after 60 minutes since said absorption started.

4. The absorbing agent composition as defined in claim 1, wherein said absorbing agent composition contains a nonvolatile water-soluble compound.

5. An absorbent material containing an absorbing agent composition having a diffusing absorbency index under pressure of 1.5 g/g·min or higher with respect to a 0.9 weight percent sodium chloride solution under a load of 20 g/cm².

6. The absorbent material as defined in claim 5, wherein said absorbent material includes at least 40 percent by weight of said absorbing agent composition.

7. The absorbent material as defined in claim 5 further containing a hydrophilic fiber.

8. An absorbent product comprising:

an absorbent layer containing an absorbent material;

a liquid permeable sheet; and a liquid impermeable sheet, said absorbent layer being sandwiched by said two sheets, said absorbent material containing an absorbing agent composition having a diffusing absorbency index under pressure of 1.5 g/g·min or higher with respect to a 0.9 weight percent sodium chloride solution under a load of 20 g/cm².

9. The absorbent product as defined in claim 8, wherein said absorbent material includes at least 40 percent by weight of said absorbing agent composition.

10. The absorbing agent composition as defined in claim 1, comprising an absorbent resin obtained by polymerizing a hydrophilic unsaturated monomer composed mainly of an acrylic acid or a salt thereof.

11. The absorbing agent composition as defined in claim 1, comprising an absorbent resin obtained by providing absorbent resin precursor particles with a crosslinking density that is higher near a surface of the particles than inside the particles, said absorbent resin precursor particles having an average particle diameter in a range between 200 μm and 600 μm and containing up to 10 wt % of particles having a diameter smaller than 106 82 m.

12. The absorbing agent composition as defined in claim 1, comprising an absorbent resin obtained by providing absorbent resin precursor particles with a crosslinking density that is higher near a surface of the particles than inside the particles, said absorbent resin precursor particles being obtained by polymerizing a hydrophilic unsaturated monomer mainly composed of acrylic acid the acid radicals of which are neutralized in a range between 50 mol % and 90 mol %.

* * * * *

UNITED STATES PATENT AND TRADEMARK OFFICE
CERTIFICATE OF CORRECTION

PATENT NO. : 5,797,893
DATED : August 25, 1998
INVENTOR(S) : Katsuyuki WADA et al.

It is certified that error appears in the above-indentified patent and that said Letters Patent is hereby corrected as shown below:

Col. 7, line 67, "600 82m" should read --600µm--.

Col. 26, line 47, "106 82m" should read --106µm--.

Col. 30, line 15, "106 82m" should read --106µm--.

Signed and Sealed this

Fifth Day of January, 1999

Attest:

Attesting Officer

*Acting Commissioner of Patents and Trademarks*